US012629126B2

(12) United States Patent
Bernhardt

(10) Patent No.: US 12,629,126 B2
(45) Date of Patent: May 19, 2026

(54) METHOD FOR PROVIDING CONTROL SETTINGS, USE OF THE CONTROL SETTINGS AND OVERALL MEDICAL SYSTEM

(71) Applicant: Siemens Healthcare GmbH, Erlangen (DE)

(72) Inventor: Philipp Bernhardt, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 246 days.

(21) Appl. No.: 18/082,018

(22) Filed: Dec. 15, 2022

(65) Prior Publication Data

US 2023/0190219 A1     Jun. 22, 2023

(30) Foreign Application Priority Data

Dec. 22, 2021     (DE) ..................... 10 2021 214 897.2

(51) Int. Cl.
| | |
|---|---|
| *A61B 6/00* | (2024.01) |
| *A61B 6/46* | (2024.01) |
| *A61B 6/50* | (2024.01) |

(52) U.S. Cl.
CPC .............. *A61B 6/545* (2013.01); *A61B 6/463* (2013.01); *A61B 6/481* (2013.01); *A61B 6/486* (2013.01); *A61B 6/542* (2013.01); *A61B 6/507* (2013.01)

(58) Field of Classification Search
None
See application file for complete search history.

(56) References Cited

U.S. PATENT DOCUMENTS

| | | | |
|---|---|---|---|
| 6,052,476 A | 4/2000 | Qian et al. | |
| 2004/0127789 A1* | 7/2004 | Ogawa ................... | A61B 6/488 |
| | | | 600/425 |

(Continued)

FOREIGN PATENT DOCUMENTS

| | | |
|---|---|---|
| DE | 19842950 A1 | 3/1999 |
| DE | 102011085618 A1 | 5/2013 |

*Primary Examiner* — Christopher Koharski
*Assistant Examiner* — Farouk A Bruce
(74) *Attorney, Agent, or Firm* — Lempia Summerfield Katz LLC

(57)     ABSTRACT

Systems and methods for a good x-ray quality with as low a radiation exposure for a patient as possible. The method provides control settings for recording a series of x-ray images by an x-ray device during a flow of contrast agent through a liquid-filled hollow organ of a patient. The method includes the following steps: selecting a frame rate f, which, with respect to the x-ray device used, contributes to at least 90% of the maximum adjustable frame rate, determining a contrast agent infusion rate R for the hollow organ, which generates a fill level of at least 75% in the hollow organ, using a vessel diameter d of the hollow organ and a flow speed v of the liquid of the hollow organ, determining an infusion duration t which represents a contrast agent bolus length as a function of the selected frame rate f, which infusion duration t generates an overlap of at most 25% between two consecutive x-ray images using the selected frame rate f, providing a first control setting in respect of the selected frame rate f for the x-ray device for recording the series of x-ray images and providing a second control setting in respect of the determined contrast agent infusion rate R and the determined infusion duration t.

9 Claims, 4 Drawing Sheets

(56)          References Cited

U.S. PATENT DOCUMENTS

| | | | |
|---|---|---|---|
| 2008/0107233 | A1 | 5/2008 | Sakaguchi et al. |
| 2008/0262346 | A1* | 10/2008 | Assis ................... A61B 5/0275 |
| | | | 600/431 |
| 2013/0109966 | A1 | 5/2013 | Assmann et al. |
| 2016/0278725 | A1 | 9/2016 | Van Nijnatten |
| 2018/0330507 | A1* | 11/2018 | Schormans .............. A61B 5/33 |
| 2019/0128988 | A1* | 5/2019 | von Samson-Himmelstjerna ....... |
| | | | G01R 33/4833 |
| 2022/0175332 | A1* | 6/2022 | Haase ................... A61B 6/504 |

* cited by examiner

Select frame rate > 90% —20

Determine contrast agent infusion rate —21

Determine the infusion duration as a function of the frame rate —22

Provide control setting frame rate —23

Provide control setting infusion rate and infusion duration —24

20 — Select frame rate > 90%

27 — Select dose per image

21 — Determine contrast agent infusion rate $$R = \frac{v \cdot d \cdot \pi}{4} \cdot x$$

$$1 < x < 0{,}75$$

— 25

22 — Determine the infusion duration as a function of the frame rate $$t = y \cdot \frac{1}{f}$$

$$0 < y < 0{,}25$$

— 26

23 — Provide control setting frame rate

24 — Provide control setting infusion rate and infusion duration

|  | Technical image quality | Contrast agent | Overall x-ray dose |
|---|---|---|---|
| "Lower overall x-ray dose" | identical | identical | -50% |
| "Less contrast agent" | identical | -30% | identical |
| "Higher image quality" | +100% | identical | identical |

METHOD FOR PROVIDING CONTROL SETTINGS, USE OF THE CONTROL SETTINGS AND OVERALL MEDICAL SYSTEM

CROSS REFERENCE TO RELATED APPLICATIONS

This application claims the benefit of DE 102021214897.2 filed on Dec. 22, 2021, which is hereby incorporated by reference in its entirety.

FIELD

Embodiments relate to a method for providing control settings for the recording of a series of x-ray images by an x-ray device during a flow of contrast agent through a liquid-filled hollow organs.

BACKGROUND

In medical diagnostics, the non-invasive representation of inner body structures and organs by x-ray imaging is a wide-spread method. In the process a high contrast may be achieved between bones and soft tissues. However, the contrast between different soft tissues is only suited to a restricted degree to the diagnostics on account of minimal absorption differences. Contrast agents are therefore applied in order to increase the contrast of specific body structures such as hollow organs (blood vessels) or body fluids, for example. These contain an element that absorbs particularly strong (or particularly weak) x-ray radiation, in order as a result to achieve a high image contrast with the surrounding tissues with a low (or average) absorption. In radiology imaging by x-ray radiation, (positive) contrast agents containing iodine or (negative) contrast agents containing carbon dioxide are currently used to represent body fluids, organs and pathological processes. The contrast agent moves as a contrast agent bolus, for example together with the blood, through the blood vessels. This flow is then monitored by a series of x-ray images, for example fluoroscopy x-ray images, with a determined, previously adjusted frame rate. The objective here is to achieve as high an image quality as possible, in order to obtain a good diagnosis and image monitoring.

The contrast agent is either injected into the blood vessel of the patient manually by a physician or by an automatically controlled injector. In this context, two parameters may be adjusted, on the one hand the concentration C of the contrast agent and on the other hand what is known as the contrast agent bolus length L (also specifiable as infusion duration t). The product of the concentration C and the bolus length L defines the quantity of contrast agent C*L injected. This quantity is a measure of the drug load for the kidneys of a patient and the objective of an examination is always to keep the quantity of contrast agent to a minimum.

With respect to the series of x-ray recordings, two parameters, namely on the one hand the frame rate f and on the other hand the x-ray dose D per image, may likewise generally be varied. Here the product D·f of the two parameters also defines the overall x-ray dose for the scene, and the objective here is also to keep the radiation exposure for the patient and personnel to a minimum.

BRIEF SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide an x-ray monitoring method, that, during a flow of contrast agent through a hollow organ, requires an x-ray dose that is particularly low as a function of the quality of the x-ray images.

The method for providing control settings for the recording of a series of x-ray images by an x-ray device during a flow of contrast agent through a liquid-filled hollow organ of a patient includes the following steps: selecting a frame rate f, that, with respect to the x-ray device used, contributes at least 90% of the maximum adjustable frame rate f, determining a contrast agent infusion rate R for the hollow organ, that generates a fill level of at least 75% in the hollow organ, using a vessel diameter d of the hollow organ and a flow speed v of the liquid of the hollow organ, determining an infusion duration t that represents a contrast agent bolus length as a function of the selected frame rate f, which infusion duration t generates an overlap of at most 25% between two consecutive x-ray images using the selected frame rate (f), providing a first control setting in respect of the selected frame rate f for the x-ray device for recording the series of x-ray images and providing a second control setting in respect of the determined contrast agent infusion rate R and the determined infusion duration t.

Using the method, an x-ray monitoring is provided during a flow of contrast agent through a hollow organ. The x-ray monitoring requires an x-ray dose that is particularly low as a function of the quality of the x-ray images. In this way, the x-ray quality may be increased or the overall x-ray dose reduced as a function of the preference of the operator or the requirements of the examination. The radiation exposure for the patient is therefore not higher when the quality of the examination increases and may even be reduced with a consistent quality. As a result, examinations and interventions for the patient and/or the personnel become safer and less strenuous. Embodiment use what is known as a "short intensive bolus", in other words as short a contrast agent bolus of high concentration as possible, in conjunction with a high frame rate, contrary to expectations a surprisingly high image quality may be achieved with a surprisingly low overall x-ray dose.

A frame rate f is a known parameter during the recording of scenes from a plurality of (for example medical) images, for example (fluoroscopy) x-ray images with an x-ray device. The frame rate f refers to the number of images per time unit (for example seconds). Known x-ray devices have in each case a maximum frame rate that may be implemented technically using the x-ray device. With a typical x-ray device this may be for example 30 Hz or 50 Hz or with particularly high-quality x-ray devices also 100 Hz. With one such known x-ray device, as high a value as possible, in other words at least 90% of the maximum adjustable frame rate (in other words for example at least 90% of 30 Hz, in other words at least 27 Hz or 90% of 50 Hz, in other words at least 45 Hz) is adjusted as the frame rate f.

According to an embodiment, the contrast agent infusion rate R, in other words the rate with which the respective contrast agent is introduced into the hollow organ (for example blood vessel) of the patient, is determined with the following $$\text{formula: } R = x \cdot \frac{v \cdot d \cdot \pi}{4},$$

wherein x assumes a value of between 0.75 and 1. The infusion rate R may be specified for example with the unit ml/s. A vessel diameter d of the hollow organ to be mapped may be gathered, estimated (for example on the basis of mean values) or calculated from the available data. Similarly, a flow speed v of the liquid (for example blood) flowing in the hollow organ may be gathered from the available data, estimated (for example on the basis of mean values) or calculated. X assumes a value of at least 0.75, for example at least 0.8, and at most 1. 0.75 indicates a fill level of at least 75% and 0.8 a fill level of 80% and 1 a fill level of 100% (complete displacement). A contrast agent bolus injected in this way may be referred to as "intensive".

According to an embodiment, the infusion duration t representing the contrast agent bolus length is determined using the following $$\text{formula: } t = \frac{y}{f}.$$

f is the frame rate and y assumes a value of between 0 and 0.25, for example less than 0.2. Using a value y of 0.25 or 0.2 or 0.1, an overlap of approx. 25% or approx. 20% or approx. 10% is produced between two consecutive x-ray images using the selected frame rate (f). The overlap may not exceed 25% and may amount for example to at most 20% or at most 10%. In this way, thus by a very short contrast agent bolus length, the overall x-ray dose may be kept to a minimum as a function of the image quality and the radiation exposure for the patient may thus be minimized.

According to an embodiment, an x-ray dose D per image is selected and is likewise provided as a control setting for the x-ray device. For example, depending on the desired x-ray quality, a relatively minimal to very minimal x-ray dose D per image may be adjusted here in order to protect the patient.

According to an embodiment, the first control setting is used to control an x-ray device for recording a series of x-ray images with the frame rate f during a flow of contrast agent with the determined contrast agent infusion rate R and the determined infusion duration t. A contrast agent injection may be applied manually (for example by an injector) for example by an operator (for example a male or female physician) according to the second control setting, for instance.

According to an embodiment, the second and the first control settings are used to control a contrast agent injection device for automatically injecting a contrast agent into a hollow organ of a patient with the determined contrast agent infusion rate R and the determined infusion duration t and for controlling an x-ray device for recording a series of x-ray images with the frame rate f during the thus controlled flow of contrast agent through the hollow organ. A system that is suited hereto is described further below.

According to an embodiment, the series of x-ray images is displayed on a display unit in order to facilitate an operator with an examination or the performance of an interventional procedure or operation.

Embodiments include a system configured to execute the afore-described control settings. The system includes an x-ray device with a control apparatus, an x-ray source and an x-ray detector. The x-ray device is configured to record a series of x-ray images with an adjustable image frequency f and an adjustable x-ray dose D per image. The system further includes a calculation unit for determining the infusion duration t as a function of the determined frame rate f of the x-ray device and to determine the contrast agent infusion rate R. The system provides the determination of optimal parameters for a series of (fluoroscopy) x-ray images using contrast agent administration, in order to achieve a particularly high image quality with a radiation exposure that is as low as possible.

Advantageously for a particularly precise dosing of the contrast agent, the system includes a contrast agent injection device with a control unit and an injector. The contrast agent injection device is configured to inject a contrast agent with a contrast agent infusion rate R and an infusion duration t into a hollow organ of a patient.

When a particularly short contrast agent bolus with a high fill level is used with a high frame rate, with a consistent quality of the recordings a considerable saving may be achieved during the overall x-ray dose. Alternatively, with a consistent overall x-ray dose, a significant increase in the image quality of the x-ray images may be achieved.

DETAILED DESCRIPTION

Figure 1:
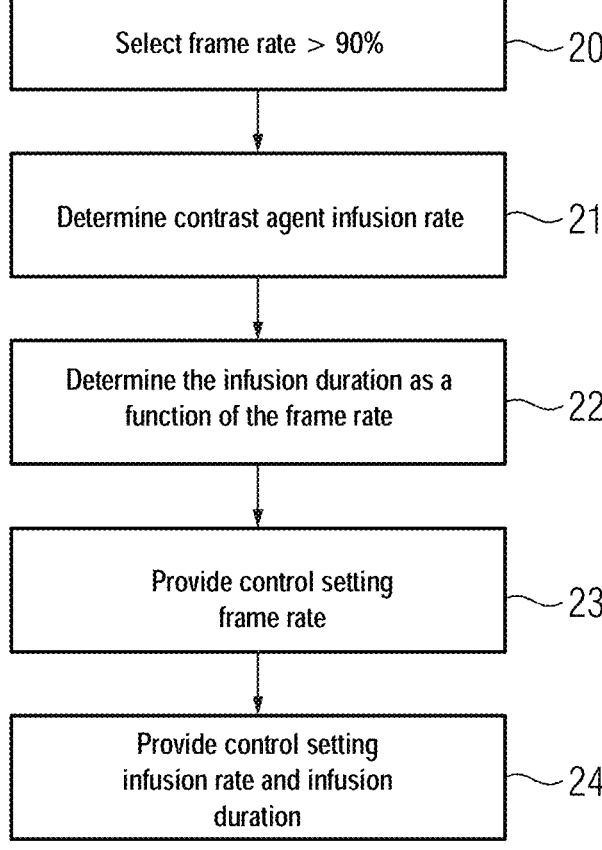
FIG. 1 depicts a sequence of steps of a method according to an embodiment.

FIG. 1 depicts a series of steps of the method for providing control settings for the recording of a series of x-ray images by an x-ray device during a flow of contrast agent through a liquid-filled hollow organ of a patient. Whereas with known recordings of a series of x-ray images during a flow of contrast agent for optimizing the corresponding parameters a thinning of the contrast agent is frequently carried out in order to reduce the patient's exposure to the contrast agent and/or the frame rate is throttled in order to reduce the overall x-ray dose, these procedures are in truth counterproductive.

The method makes use of what is known as a "short intensive bolus", in other words as short a contrast agent bolus of high concentration as possible, in conjunction with a high frame rate, which contrary to expectations provides where a surprisingly high image quality may be achieved with a surprisingly low overall x-ray dose.

Figure 4:
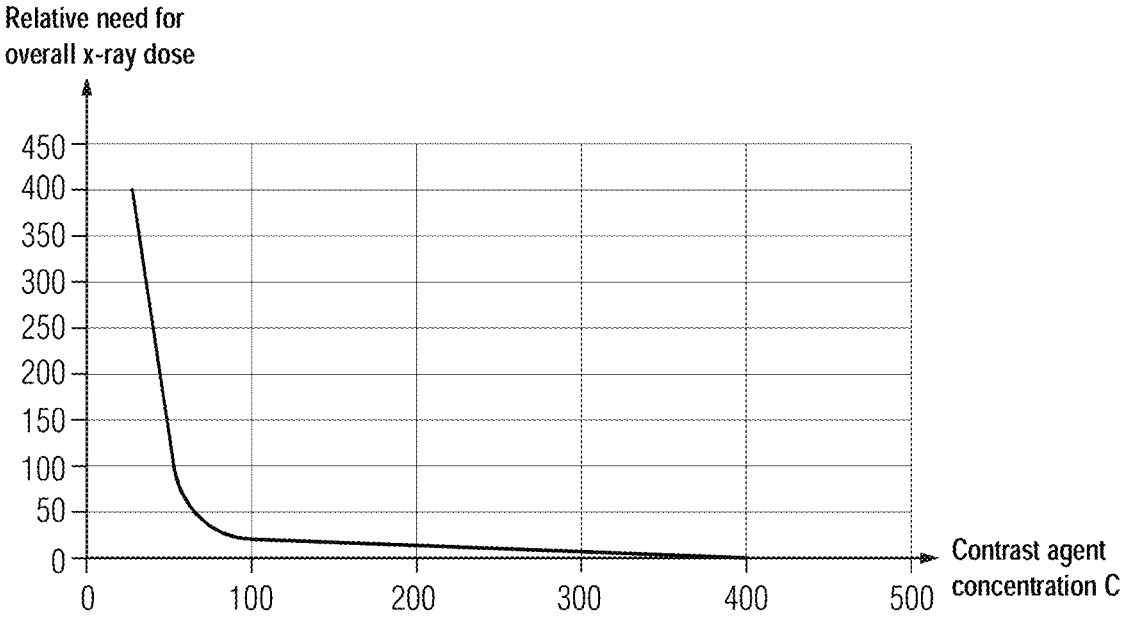
FIG. 4 depicts a graphic with a relationship between the overall x-ray dose and contrast agent concentration with the same image quality of an x-ray recording according to an embodiment.
Figures 5, 6:
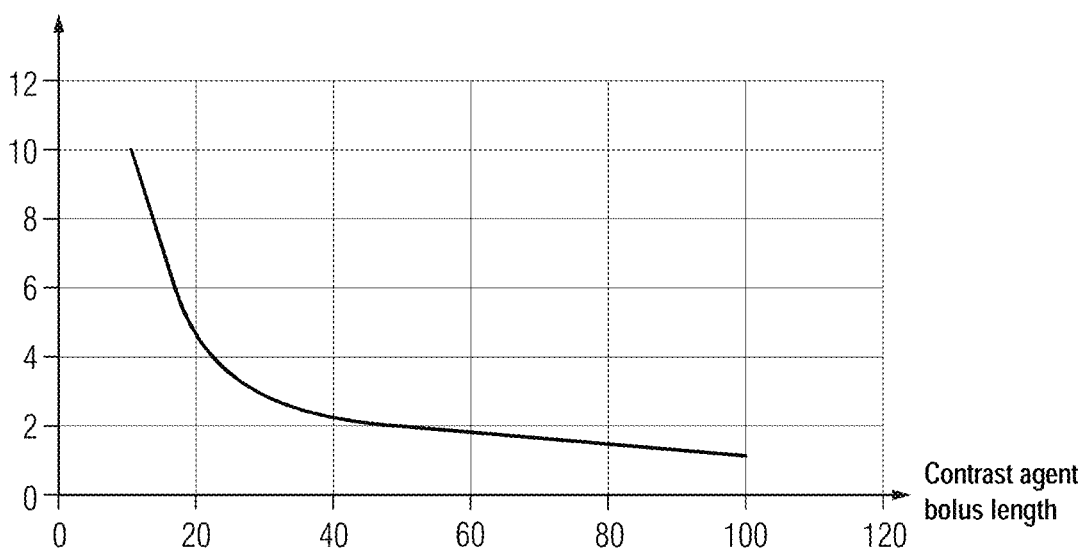
FIG. 5 depicts a graphic with a relationship between the overall x-ray dose and contrast agent bolus length with the same image quality of an x-ray recording according to an embodiment.
FIG. 6 depicts a table with a relationship between the image quality, the quantity of contrast agent and the overall x-ray dose according to an embodiment.

FIG. 4 depicts a (calculated or simulated) relationship between an overall x-ray dose and a contrast agent concentration (for example iodine content in a contrast agent containing iodine, for example specifiable in mgI/ml) with a constant image quality of the respective x-ray recording. FIG. 5 depicts a (calculated or simulated) relationship between the overall x-ray dose and the contrast agent bolus length (for example specifiable in mm) with a constant image quality of the respective x-ray recording.

One comparison of the two graphics depicts that the dependency of the overall x-ray dose on the concentration is significantly higher than the dependency on the bolus length. For this reason, the image quality efficiency is higher by a "short intensive bolus" with respect to the overall x-ray dose and/or contrast agent.

This may also be identified using the three scenarios shown in the table in FIG. 6, "lower overall x-ray dose", "less contrast agent" and "higher image quality", that are derived below by example calculations. Based on a first contrast agent concentration $C_0$, a first contrast agent bolus length $L_0$($L=v \cdot t$, where v is the flow speed of the liquid, such as blood for example, and t is the infusion duration), a first x-ray dose Do per image and a first frame rate $f_0$, the first technical image quality $C_0^2 \cdot D_0$, the first contrast agent quantity $C_0 \cdot L_0$ used and the first overall x-ray dose contribute to the scene $D_0 \cdot f_0$.

If in a first scenario ("lower overall x-ray dose") a second contrast agent concentration $C_1=2 \cdot C_0$ that is twice as high, a second contrast agent bolus length $L_1=0.5 \cdot L_0$, a second x-ray dose $D_1=0.25 \cdot D_0$ per image and a second frame rate $f_1=2 \cdot f_0$ are then assumed, the second technical image quality $C_0^2 \cdot D_0$ and the second contrast agent quantity $C_0 \cdot L_0$ used remain identical to the respective first image quality and the contrast agent quantity used and the second overall x-ray dose of the scene ($0.5 \cdot D_0 \cdot f_0$) amounts to half of the first overall x-ray dose.

If in a second scenario ("less contrast agent") a third contrast agent concentration $C_2=1.4 \cdot C_0$, a third contrast agent bolus length $L_2=0.5 \cdot L_0$, a third x-ray dose $D_2=0.5 \cdot D_0$ per image and a third frame rate $f_2=2 \cdot f_0$ are then used, the third technical image quality $C_0^2 D_0$ remains identical to the first image quality, the third contrast agent quantity $0.7 \cdot C_0 L_0$ used reduces by 30% compared with the first contrast agent quantity used and the third overall x-ray dose of the scene remains identical to the first overall x-ray dose $D_0 f_0$.

If in a third scenario ("higher image quality") a fourth contrast agent concentration $C_3=2 \cdot C_0$, a fourth contrast agent bolus length $L_3=0.5 \cdot L_0$, a fourth x-ray dose $D_3=0.5 \cdot D_0$ per image and a fourth frame rate $f_3=2 \cdot f_0$ are then used, the fourth technical image quality $2 \cdot C_0^2 D_0$ doubles compared with the first image quality and the fourth contrast agent quantity $C_0 \cdot L_0$ used remains identical compared with the first contrast agent quantity used and the fourth overall x-ray dose of the scene remains identical compared with the first overall x-ray dose $D_0 \cdot f_0$.

With the corresponding scenarios, it is assumed for the sake of simplicity that vessel movements are not present or are compensated for at the software end, moreover image averagings are also not included.

In a first step 20 of the method for providing control settings for the recording of a series of x-ray images by an x-ray device during a flow of contrast agent through a liquid-filled hollow organ of a patient, a frame rate f is selected that amounts to at least 90% of the maximum adjustable frame rate with respect to the x-ray device used. A frame rate f is a known parameter in conjunction with the recording of image series (scenes) from a plurality of (for example medical images), for example with an x-ray device for recording (fluoroscopy) x-ray images. The frame rate f refers to the number of images per time unit and is frequently specified in (1/s). Known x-ray devices includes in each case a maximum frame rate that may be implemented technically using the x-ray device. With a typical x-ray device this may be for example 30 Hz or 50 Hz or with particularly high-quality x-ray devices also 100 Hz. Within the scope of the method, as high a value as possible, in other words at least 90% of the maximum adjustable frame rate (in other words for example at least 90% of 30 Hz, in other words at least 27 Hz or at least 90% of 50 Hz, in other words at least 45 Hz, or at least 90% of 100 Hz, in other words at least 90 Hz) is adjusted as the frame rate f. The selection may be carried out either manually by a user input or automatically, for example by an algorithm executed on a control unit.

In and eighth step 27, an x-ray dose D per image is selected. For instance, depending on the desired x-ray quality a relatively low to very low x-ray dose D per image may be adjusted to protect the patient. This selection may also be carried out manually or automatically.

In a second step 21, a contrast agent infusion rate R is determined for the hollow organ, that generates a fill level of at least 75%, for example at least 80% in the hollow organ. In this context the fill level of for example 75% or 80% is understood to mean that a 75% or 80% displacement of the blood takes place. In this way, the contrast approaches the saturation, for example if the contrast agent is iodine. In order to determine the contrast agent infusion rate R, the vessel diameter d (for example in mm) of the hollow organ, in which the contrast agent is to be introduced, and a flow speed v (for example in mm/s) of the liquid of the hollow organ is used, for instance. According to an embodiment, the contrast agent infusion rate R, in other words the rate with which the respective contrast agent is introduced into the hollow organ (for example blood vessel) of the patient, is determined with the following formula:

$$R = x \cdot \frac{v \cdot d \cdot \pi}{4}.$$

Figure 2:
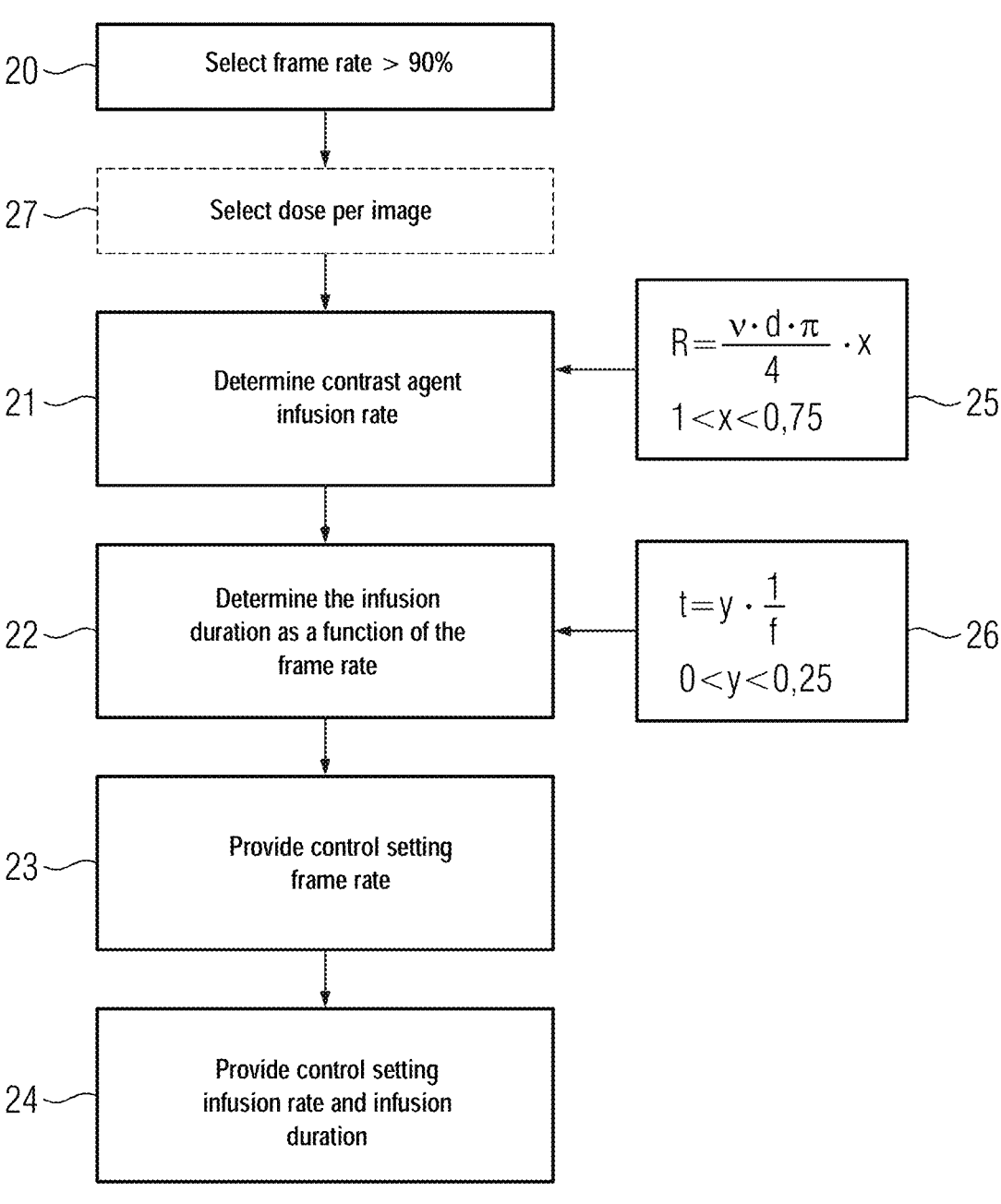
FIG. 2 depicts a sequence of steps of the method combined with usable formulas according to an embodiment.

This is shown in FIG. 2 as the sixth step 25. Here x assumes a value of between 0.75 and 1. The infusion rate R may be specified for example with the unit ml/s. A vessel diameter d of the hollow organ to be mapped may be gathered, estimated (for example on the basis of mean values) or calculated from the available data. Similarly, a flow speed v of the liquid (for example blood) flowing in the hollow organ may be gathered, estimated (for example on the basis of mean values) or calculated from the available data. X amounts to at least 0.75, for example at least 0.8, and at most 1, wherein 0.75 indicates a fill level of at least 75% and 0.8 a fill level of 80% and 1 a fill level of 100% (complete filling of the hollow organ at this point).

In a third step 22, an infusion duration t (unit in s for example) that represents a contrast agent bolus length L is determined as a function of the selected frame rate f. The infusion duration t generates an overlap of at most 25% between two consecutive x-ray images using the selected frame rate f. In this way, the contrast agent bolus length is configured to be particularly short, an overall x-ray dose (in relation to the image quality) is saved, and the radiation exposure for the patient and/or operator is reduced. For example, as shown in the seventh step 26 in FIG. 2, the infusion duration t representing the contrast agent bolus length is determined according to the relationship $$t = \frac{y}{f},$$

7 where y assumes a value of between 0 and 0.25, for example 0.2 or less. In this context, an overlap of approx. 25% or approx. 20% or approx. 10% is produced between two consecutive x-ray images using the selected frame rate f by a value y of 0.25 or 0.2 or 0.1. The overlap may not exceed 25% and may amount for example to at most 20% or at most 10%.

Then first and second control settings for further processing and execution are provided at the steps of selecting the frame rate and for x-ray dose per image and for determining infusion duration and infusion rate.

Therefore, in a fourth step 23 for the x-ray device, a first control setting is provided in respect of the selected frame rate f for recording the series of x-ray images. In addition, the optionally selected x-ray dose D per image may likewise also be provided within the scope of the first control setting for the x-ray device. The first control setting may then be used to control the x-ray device accordingly.

Moreover, in a fifth step 24, a second control setting is provided in respect of the previously determined contrast agent infusion rate R and the previously determined infusion duration t. This second control setting may then be used either for a corresponding manual or an automatic application of a contrast agent. A contrast agent injection may be applied manually for example by an operator (for example a male or female physician) according to the settings by an injector. Alternatively, a contrast agent injection device may be controlled automatically according to the control settings in order to inject a contrast agent into a hollow organ of a patient.

Figure 3:
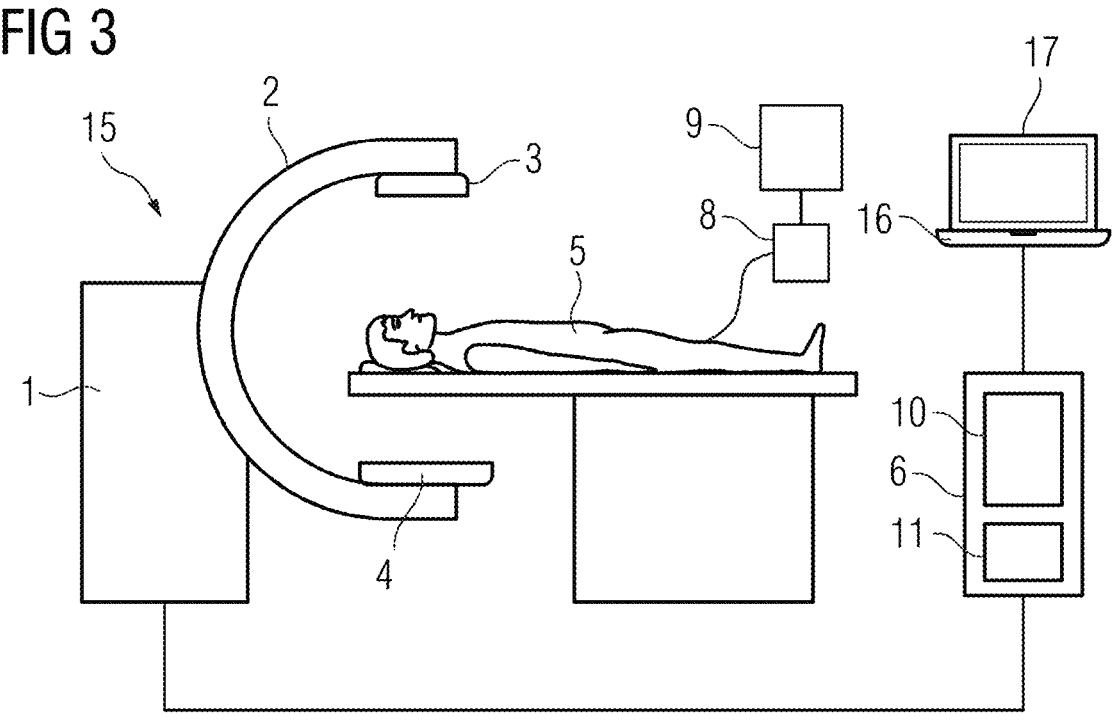
FIG. 3 depicts a view of a system for carrying out the method according to an embodiment.

FIG. 3 depicts a system 15 that is configured to execute at least one part of the above-described control settings. The system 15 has an x-ray device 1 with a control apparatus 6, an x-ray source 3 and an x-ray detector 4. The x-ray source 3 and the x-ray detector 4 are arranged on movable C-arms 2 for instance. The control apparatus is configured to control the x-ray device 1 for recording a series of (fluoroscopy) x-ray images with an adjustable image frequency f and an adjustable x-ray dose D per image.

The system 15 includes a calculation unit 10 for determining the infusion duration t as a function of the determined frame rate f of the x-ray device and for determining the contrast agent infusion rate R. The calculation unit 10 may be integrated for example in the control apparatus 10, for example in the form of a PCs or processor. In addition, a storage unit 11 may be provided. Moreover, an input unit 17 for accepting user inputs is available (for example keyboard, smart device, touch pad, microphone etc.) and a display unit 16 for displaying x-ray images, for example a monitor, projector or smart device.

For a particularly precise dosing of the contrast agent, the system 15 includes a contrast agent injection device with an injector control unit 9 and an injector 8. The contrast agent injection device is configured to inject a contrast agent with a contrast agent infusion rate R and an infusion duration t into a hollow organ of a patient.

The selected and/or determined and/or calculated control settings may be used to control the x-ray device and the contrast agent injection device. For this purpose, a control algorithm may also be used, for instance. By the method presented here, the x-ray quality may be increased or the overall x-ray dose reduced as a function of the preference of the operator or the requirements of the examination. The radiation exposure for the patient is therefore not higher when the quality of the examination increases and may even be reduced with a consistent quality. As a result, examinations and interventions for the patient and/or the personnel become safer and less strenuous.

Embodiments provide a particularly good x-ray quality with as low a radiation exposure for a patient as possible. Embodiments include a method for providing control settings for recording a series of x-ray images by an x-ray device during a flow of contrast agent through a liquid-filled hollow organ of a patient. The method includes the following steps: selecting a frame rate f, that, with respect to the x-ray device used, contributes at least 90% of the maximum adjustable frame rate f, determining a contrast agent infusion rate R for the hollow organ, that generates a fill level of at least 75% in the hollow organ, using a vessel diameter d of the hollow organ and a flow speed v of the liquid of the hollow organ, determining an infusion duration t that represents a contrast agent bolus length as a function of the selected frame rate f, which infusion duration t generates an overlap of at most 25% between two consecutive x-ray images using the selected frame rate f, providing a first control setting in respect of the selected frame rate f for the x-ray device for recording the series of x-ray images and providing a second control setting with respect to the determined contrast agent infusion rate R and the determined infusion duration (t).

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing control settings for recording a series of x-ray images by an x-ray device during a flow of contrast agent through a blood vessel of a patient, the blood vessel filled with a liquid, the method comprising:

identifying a maximum frame rate of the x-ray device;

identifying a vessel diameter of the blood vessel and a flow speed of the liquid in the blood vessel;

selecting a frame rate for the x-ray device that is at least 90% of the maximum frame rate of the x-ray device;

determining, based on the vessel diameter of the blood vessel and the flow speed of the liquid of the blood vessel, a contrast agent infusion rate for the blood vessel, that generates a fill level of at least 75% in the blood vessel;

determining an infusion duration representing a contrast agent bolus length as a function of the selected frame rate, wherein the infusion duration generates an overlap of at most 25% between two consecutive x-ray images using the selected frame rate;

providing a first control setting in respect of the selected frame rate for the x-ray device for recording the series of x-ray images;

providing a second control setting in respect of the determined contrast agent infusion rate and the determined infusion duration; and injecting, by a contrast agent injection device, the contrast agent according to the second control setting in respect of the determined contrast agent infusion rate and the determined infusion duration into the blood vessel of the patient.

2. The method of claim 1, wherein the contrast agent infusion rate is determined using the following formula: contrast agent infusion rate=$x \cdot (v \cdot d \cdot \pi)/4$, wherein v is the flow speed, d is the vessel diameter, and x comprises a value of between 0.75 and 1.

3. The method of claim 1, wherein the infusion duration representing the contrast agent bolus length is determined with the following formula: infusion duration=$y/f$, wherein f is the selected frame rate and y comprises a value of between 0 and 0.25.

4. The method of claim 1, wherein an x-ray dose per image is selected and provided as the first control setting for the x-ray device.

5. The method of claim 1, further comprising:

using the first and second control settings to control the x-ray device for recording a series of x-ray images with the frame rate during a contrast agent flow with the determined contrast agent infusion rate and the determined infusion duration.

6. The method of claim 5, further comprising:

displaying the series of x-rays on a display unit.

7. The method of claim 1, further comprising:

using the first and second control settings to control a contrast agent injection device configured for injecting a contrast agent into the blood vessel of a patient with the determined contrast agent infusion rate and the determined infusion duration and to control an x-ray device configured for recording a series of x-ray images with the frame rate during the flow of contrast agent through the blood vessel.

8. The method of claim 7, further comprising:

displaying the series of x-rays on a display unit.

9. A system comprising:

an x-ray device including a control apparatus, an x-ray source, and an x-ray detector, wherein the x-ray device is configured to record a series of x-ray images with an adjustable image frequency and an adjustable x-ray dose per image, wherein the x-ray device includes a maximum frame rate;

a calculation unit configured to:

select a frame rate that, with respect to the x-ray device used, amounts to at least 90% of the maximum adjustable frame rate of the x-ray device;

determine a contrast agent infusion rate for a blood vessel of a patient based on an identified vessel diameter of the blood vessel and an identified flow speed of a liquid through the blood vessel, that generates a fill level of at least 75% in the blood vessel;

determine an infusion duration representing a contrast agent bolus length as a function of the selected frame rate, wherein the infusion duration generates an overlap of at most 25% between two consecutive x-ray images using the selected frame rate; and provide a first control setting in respect of the selected frame rate for the x-ray device for recording the series of x-ray images and a second control setting in respect of the determined contrast agent infusion rate and the determined infusion duration;

wherein the first control setting are used by the control apparatus to control the x-ray device; and a contrast agent injection device including a control unit and an injector, wherein the contrast agent injection device is configured to inject a contrast agent according to the second control setting into the blood vessel of the patient.

* * * * *